United States Patent
Fischer et al.

(10) Patent No.: US 6,406,633 B1
(45) Date of Patent: Jun. 18, 2002

(54) FRACTION COLLECTION DELAY CALIBRATION FOR LIQUID CHROMATOGRAPHY

(75) Inventors: Steven M. Fischer, Hayward; Glen F. Ingle, Sunnyvale, both of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 160 days.

(21) Appl. No.: 09/611,148

(22) Filed: Jul. 6, 2000

Related U.S. Application Data

(62) Division of application No. 09/393,595, filed on Sep. 10, 1999, now Pat. No. 6,106,710.

(51) Int. Cl.[7] ............................................... B01D 15/08
(52) U.S. Cl. ..................... 210/659; 210/85; 210/143; 210/198.2; 436/161; 73/61.57
(58) Field of Search .................. 210/635, 656, 210/659, 198.2, 143; 422/70; 436/161; 73/61.52, 61.55, 61.57

(56) References Cited

U.S. PATENT DOCUMENTS

| | | | | | |
|---|---|---|---|---|---|
| 3,996,017 A | * | 12/1976 | Kaiser | ..................... | 210/198.2 |
| 4,269,710 A | * | 5/1981 | Hunt | ....................... | 210/198.2 |
| 4,654,052 A | * | 3/1987 | Sharp | ...................... | 210/198.2 |
| 5,227,135 A | * | 7/1993 | Godec | ......................... | 422/98 |
| 5,234,586 A | * | 8/1993 | Afeyan | ..................... | 210/198.2 |
| 5,306,426 A | * | 4/1994 | Afeyan | ....................... | 210/635 |
| 5,310,683 A | * | 5/1994 | Godec | ......................... | 436/123 |
| 5,330,714 A | * | 7/1994 | Godec | ........................... | 422/52 |
| 5,476,000 A | * | 12/1995 | Henderson | ................. | 73/23.07 |
| 5,888,863 A | * | 3/1999 | Abubaker | ................... | 204/452 |

* cited by examiner

Primary Examiner—Ernest G. Therkorn

(57) ABSTRACT

A fraction collection system for liquid chromatography includes a conduit, which directs a sample eluent from an LC column through a flow splitter to a destructive analytical detector such as a mass spectrometer to analyze sample components, and to a fraction collector. A nondestructive detector such as a photodetector is positioned near the fraction collector to detect arrival of sample components. Optionally, a nondestructive detector such as a photodetector is situated upstream from the splitter, to detect passing sample components. Time intervals between detection of a calibrant or a sample component at any two of the detectors provide for automatable identification of selected sample components at the sample collector.

2 Claims, 4 Drawing Sheets

FRACTION COLLECTION DELAY CALIBRATION FOR LIQUID CHROMATOGRAPHY

CROSS REFERENCE TO RELATED APPLICATION(S)

This is a divisional of application Ser. No. 09/393,595 filed on Sep. 10, 1999, now U.S. Pat. No. 6,106,710.

FIELD OF THE INVENTION

This invention relates to liquid chromatography ("LC") and, particularly, to fraction collection in liquid chromatography.

Background Compounds may be collected as they elute from liquid chromatographic columns ("LC columns") and then subjected to further analysis as, for example, by mass spectrometry ("MS"). For complex mixtures, the chromatographic column may be coupled directly with a mass spectrometer or other analytical apparatus. Where LC and MS are carried out as a unified, continuous process, it is known as liquid chromatography/mass spectrometry ("LC/MS").

Typically the effluent from the LC column is in a highly dilute liquid phase, with the separated components emerging from the LC column as "peaks" entrained within a liquid carrier. This can present significant problems for efficiently coupling the effluent with the ion source of the mass spectrometer. Nonvolatile inorganic components present in the eluent, for example as buffers, can interfere with ionization, and where gradient elution is employed the composition of the solvent changes in the course of the analysis. Typical flow rates of LC eluents produce, after vaporization, the equivalent of gas flows much too high for conventional ion sources to accommodate. The difficulty of removing the liquid solvent from the components to be analyzed in the mass spectrometer has raised significant challenges for the development of LC/MS systems.

Generally, in a conventional LC/MS analysis, the sample to be analyzed is separated using an LC column, and the eluent is directed to the mass spectrometer, which completely consumes the sample stream. Optionally, the LC eluent may be passed through a nondestructive detector, such as an optical detector, to provide general information as to the presence of peaks in the flow, without destroying the sample in the stream, before the sample stream is sent on to the MS. Optical detectors conventionally include, for example, UV-Vis, Refractive Index, and fluorescence detectors.

It may be desirable to employ a fraction collection system, to physically collect a purified sample or samples from a mixture in the LC eluent stream. In one conventional approach, a nondestructive detector is employed upstream from the fraction collector, and the time delay between the moment a peak is detected at the detector and the time of arrival of the peak at the fraction collector is calculated from the known or estimated flow rate and the measured or calculated volume capacity of the tubing and connections between the detector and the fraction collector. This calculated time delay provides a basis for an expectation of when a component of the sample, detected at the nondestructive detector, should arrive at the collection vessel. The sample component is presumed to be contained in a collection vessel that received the eluent flow at the estimated arrival time, and the material in that collection vessel can be selected for further analysis.

SUMMARY

In one approach to fraction collection, the eluent stream is split so that the sample stream can be subject to destructive analysis without consuming the sample. In a mass-based fraction collection system, for example, a portion of the sample stream is sent to a mass detector to detect the presence of a sample, identifiable by specific ions or ion signals, and the rest of the stream is sent to the fraction collector. According to the invention the time a sample component is detected at the destructive detector (MS in a mass-based system) is used to predict when the stream containing that sample component should arrive at the fraction collector, permitting accurate and reliable placement of the purified sample component in an identified collection vessel or further sample stream for further analysis.

In one aspect the invention features fraction collection apparatus including a first conduit connected at its upstream end to the outlet from a liquid chromatography column and connected at its downstream end to the inlet of a flow splitter, a second conduit connected at its upstream end to a first outlet from the flow splitter and connected at its downstream end to a sample collector, and a third conduit connected at its upstream end to a second outlet from the flow splitter and connected at its downstream end to a destructive detector; a first nondestructive detector is configured near the sample collector to detect passage of a sample component in the third conduit and, optionally, a second nondestructive detector is situated upstream from the splitter to detect passage of a sample component in the first conduit.

In some embodiments the destructive detector is a mass spectrometer or an evaporative light scattering detector or an electrochemical detector. In some embodiments each or both of the first and the second non-destructive detector is an optical detector, such as a UV-Vis absorption detector, a fluorescence detector, or a refractive index detector. In some embodiments the conduits comprise tubing or channels formed in a solid substrate; where an optical detector is employed as a nondestructive detector the conduit preferably is constructed of a material that permits transmission of the wavelength (UV, visible) or wavelengths employed in the detection.

In some embodiments the fraction collection apparatus further includes a fourth conduit connected at its upstream end to a third outlet from the flow splitter and connected at its downstream end to a quantitative detector. In still other embodiments having a fourth conduit connected at its downstream end to a quantitative detector, the apparatus further includes a second splitter having an inlet and a first outlet connected inline in either the second conduit or the third conduit, and a second outlet connected to the upstream end of the fourth conduit. In some embodiments the quantitative detector includes an evaporative light-scattering detector or a nitrogen-sulfur detector.

In some embodiments the fraction collection apparatus is operatively connected to automated controls which, in particular embodiments, receive and process data respecting the detection times at the destructive detector and at one or both of the nondestructive detectors. Preferably the automated controls include a computer capable of receiving signals from the detectors and determining intervals between arrival times, and preferably the automated controls are further capable of employing the time interval data dynamically to activate and control the collection of particular fractions.

In another aspect the invention features a method for collecting a sample component in a sample stream, by dividing the sample stream into a first stream passing into a destructive detector and a second stream passing to a sample collector, introducing a calibrant into the sample stream and determining the difference in time $T_D$ between the detection of the calibrant at the destructive detector and detection of the calibrant at a nondestructive detector near the sample collector, then detecting the sample component in the first stream using the destructive detector and determining the time $T_2$ the sample component was detected by the destructive detector, and collecting the sample component at a time $T_3$ equivalent to $T_D+T_2$.

In still another general aspect the invention features a method for calibrating an expected time of arrival at a collector of a sample component in a sample stream from an LC column, by dividing the sample stream into a first stream passing to a destructive detector and a second stream passing to a sample collector, introducing a calibrant into an eluent stream and determining the difference in time $T_D$ between the detection of the calibrant at the destructive detector and detection of the calibrant at a nondestructive detector near the sample collector, whereby a sample component introduced into a similar eluent stream and detected at the destructive detector at a time $T_2$ is expected to arrive at the sample collector at a time $T_D$ later than $T_2$.

DETAILED DESCRIPTION

Figure 1:
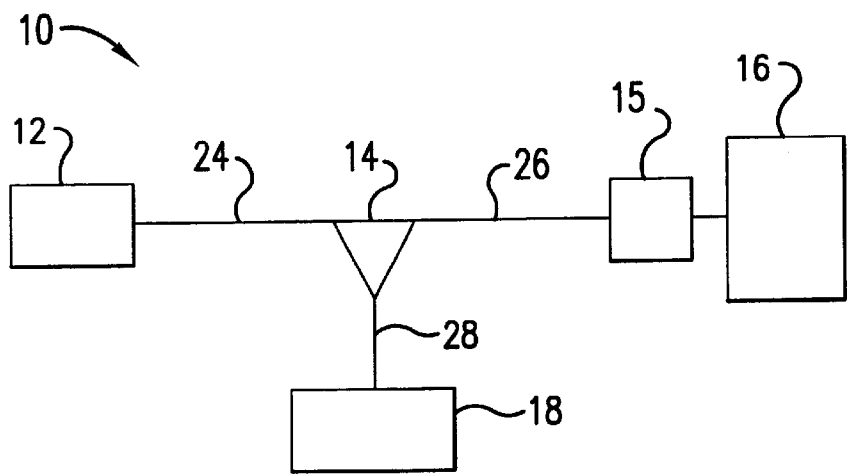
FIG. 1 is a flow path diagram showing arrangement of components of exemplary fraction collection delay calibration apparatus according to the invention.

Referring now to FIG. 1, there is shown diagrammatically a system flow path generally indicated at 10. Briefly, the eluent stream, carrying a series of separated sample components, passes by force of a pump (not shown in the FIGS.) from the LC column 12 to a stream splitter 14, which directs the eluent stream in part to a destructive detector 18 (the analysis stream) and in part to a fraction collector 16 (the collection stream). Downstream from the splitter 14, while the flow volume in the analysis stream may be different from the flow volume in the collection stream, all the separated sample components are present in both the collection stream and the analysis stream, in undisturbed sequence and in proportionate amounts. The destructive detector 18, which may be, for example, a mass spectrometer, analyzes the series of components as they arrive in the analysis stream. As the collection stream passes from splitter 14 toward fraction collector 16 it passes a nondestructive flow detector 15, situated near the fraction collector 16. The nondestructive flow detector 15 detects the presence of the components in the series as they pass.

Figure 2:
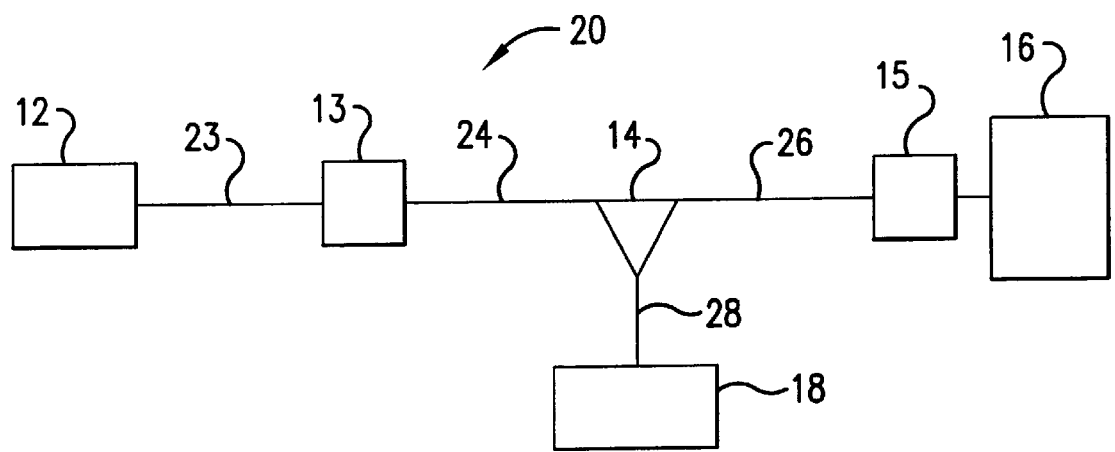
FIG. 2 is a flow path diagram showing arrangement of components of alternative exemplary fraction collection delay calibration apparatus according to the invention.

With reference now to FIG. 2, in which like components have reference numerals as in FIG. 1, the system may have an additional nondestructive detector 13 upstream from the splitter 14. As the components in the eluent stream pass from LC column 12 to splitter 14, they pass nondestructive detector 13, which detects sample components as they are carried through in the eluent stream.

The destructive analytical detector 18 may be a mass spectrometer, an evaporative lights-scattering detector ("ELSD"), or an electrochemical detector.

The flow detector 15 at the fraction collector may be any nondestructive detector, and an optical detector (detecting changes in absorption or fluorescence as the eluent stream passes the detector) may be particularly useful. Suitable optical detectors include UV-Vis, Refractive Index, and fluorescence detectors. For example, a suitable absorption detector includes a photodetector illuminated by a light emitting diode ("LED") and oriented so that the eluent stream passes between the light source and the photodetector. The presence of sample components in the eluent stream causes changes in the absorption characteristics in the eluent stream, detectable by the photodetector as a series of absorption peaks as the sample stream flows through. The particular wavelength or wavelengths of light used to illuminate the eluent stream, and the particular wavelengths detected, may be selected according to the sort of sample components sought to be detected. The upstream detector 13, where present, may also be any nondestructive detector and, as for the fraction collector flow detector, an optical detector may be particularly useful.

The conduits 23, 24, 26, 28 through which the sample stream passes may be constructed of any material suitable for flow systems for chemical analysis, and of any dimensions suitable for the desired flow rates, including materials and dimensions known in the chemical analysis arts, and particularly known in the automated chemical analysis arts. The conduits may, for example, be tubing, and may be constructed of a plastic, such as, for example, Teflon® or Tefzel®. Where photodetectors are employed as nondestructive detectors, upstream from the splitter or at the fraction collector, a transparent plastic (or a plastic that permits passage of light of the particular illuminating and detected wavelengths) may be employed to convenience: the light source (e.g., LED) and the photodetector may simply be disposed on either side of the conduit at a desired point. Or, the conduits may be formed by molding or cutting or machining a substrate and, particularly where very small dimensions are desired for the system, the conduits may be formed in a planar substrate (typically of glass or a plastic), according to the microfluidics art.

The splitter may be a simple "Y", or a valve. To reduce remixing or peak broadening in the separated sample components, the splitter should be constructed with flow channels having diameters and constrictions configured and dimensioned to accommodate and direct the flow at the rates used, as can be readily determined by those of ordinary skill in the art. The splitter may alter the flow rates in both downstream flowpaths in a non-deterministic manner, and so a simple volume-flow rate calculation cannot be relied upon. And system flow rates, including the split ratio, may differ for different solvents (for example, different solvents may have different viscosities), and may vary over the course of a LC gradient run. Accordingly, it is useful to be able to measure actual delay times readily and routinely in the course of a run.

As will be appreciated, the respective components of the separated sample typically will have different arrival times at the destructive detector 18 and at the fraction collector 16. Particularly, for example, if the fluid volume within the system between the splitter 14 and the destructive detector 18 (the analytical stream) is less than that between the splitter 14 and the fraction collector 16 (the collection stream), the sample components can be expected to arrive at the fraction collector at a time later than at the destructive detector. If this delay interval $T_D$ is known or can be calibrated, then a particular sample component X, identified at the destructive detector 18 at a given time $T_x$, can be expected to arrive at the fraction collector at a time $T_x$ plus $T_D$. The fraction collector flow detector may be situated at a point very close to the fraction collector, so that the time interval between detection at the fraction collector flow detector and arrival in the collection vessel is very small and varies only minutely. An aliquot of the sample stream containing sample component X can be selectively collected by causing the fraction collector to collect an aliquot from the sample stream at the expected arrival time; or, where the sample collector is continually collecting aliquots in the sample stream, the particular aliquot that is collected at the expected arrival time can be identified as containing component X.

In a system as illustrated in FIG. 1, the delay interval can be calibrated by inserting into the sample stream a calibrant that is particularly identifiable both in the destructive detector and by the fraction collector flow detector, and measuring or recording the respective arrival times. Where an upstream nondestructive detector is employed, as illustrated in FIG. 2, an additional time data point is provided. During a calibration run, the calibrant is injected into the eluent stream at a time $T_0$; it first passes the upstream detector 13, and is there detected a time $T_1$, and may be recorded as a peak; then it passes through the splitter and at some later time $T_2$ a portion of calibrant, carried in the analytical stream is detected and may be recorded at the destructive detector 18; and then at a still later time $T_3$ the remainder of the calibrant is detected and may be recorded as a peak by the fraction collection flow detector 15.

Figure 3A:
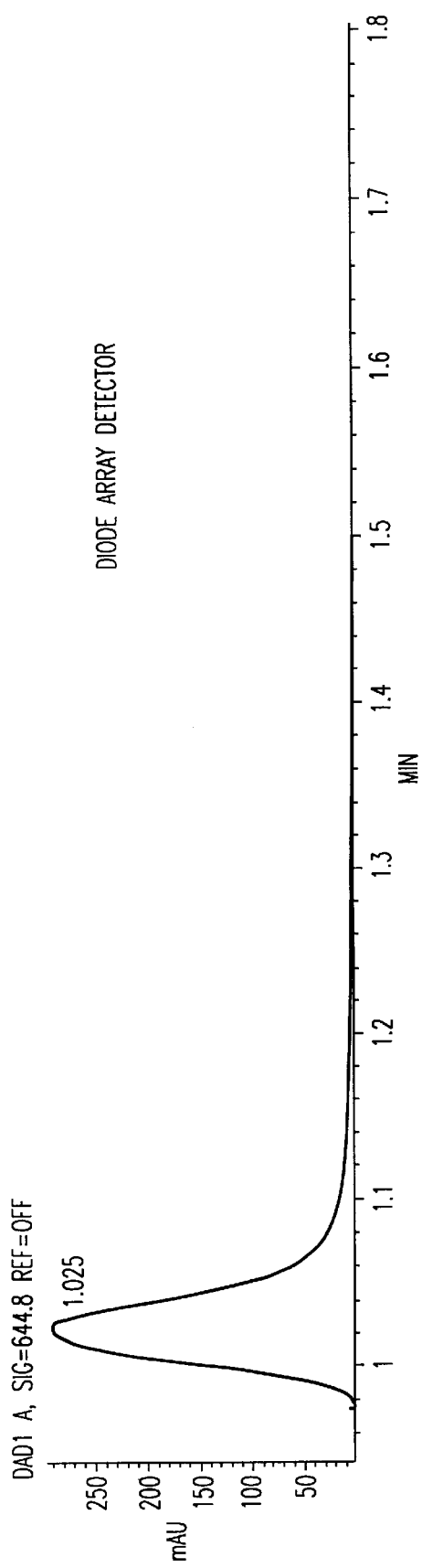
FIGS. 3A, 3B, and 3C show signals produced at the upstream detector, the destructive detector, and the downstream nondestructive detector, showing detection of a sample component according to the invention.
Figure 3B:
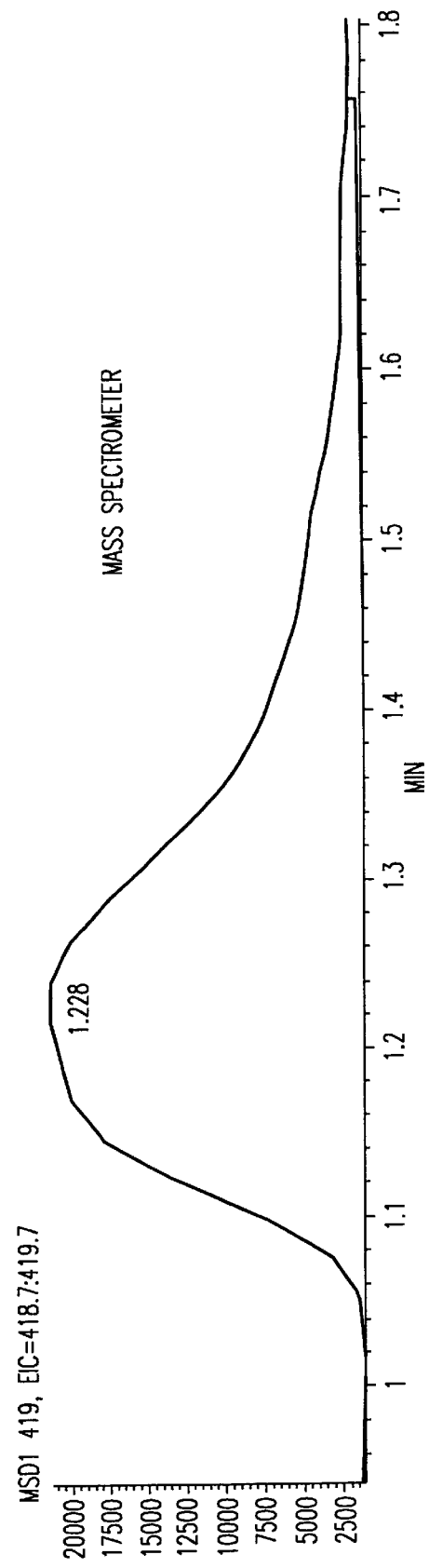
Figure 3C:
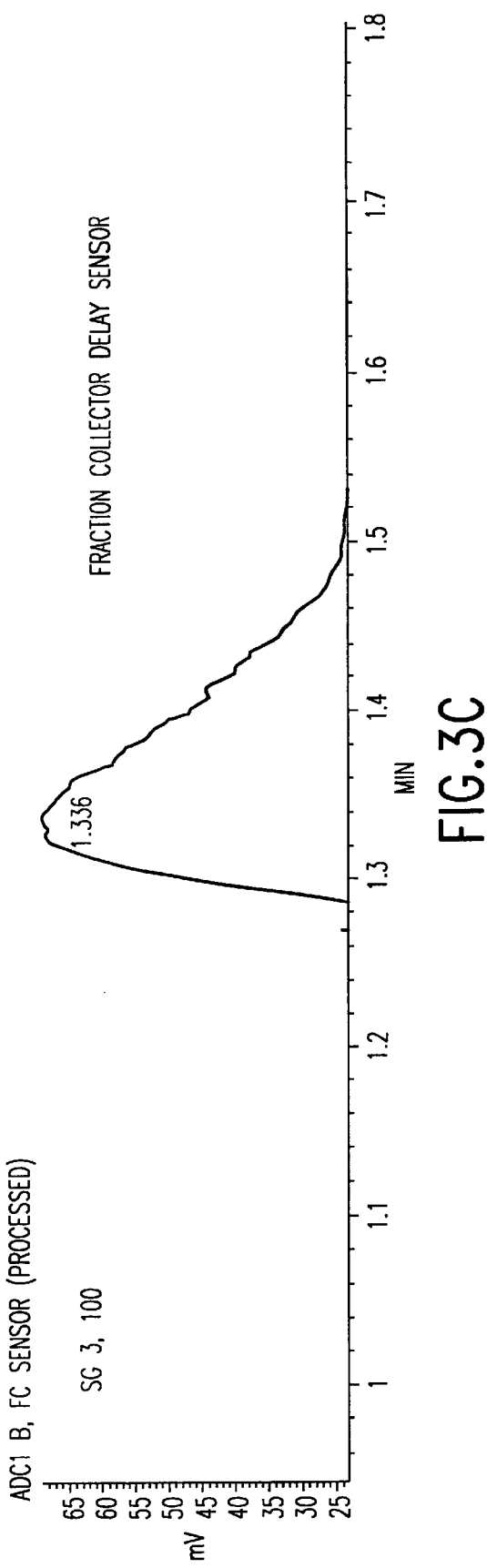

FIG. 3 shows data for a single component calibrant during a run through a system as in FIG. 2. The upper curve is a chromatogram from the upstream detector (a UV-Vis absorption detector in this example), the middle curve is a recording from the destructive detector (a Hewlett-Packard LC/MSD G1946B mass spectrometer in this example), and the lower curve is a chromatogram from the fraction collector flow detector (in this example employing an LED (HP HLMP-Q106) emitting light at 640 nanometers and a silicon NPN phototransistor (Siemens BPX-81) suitable for wavelength detection in the range 440 to 1070 nanometers. For this particular system configuration, and at the flow rate for this particular run the time $T_1$ (as measured at maximum peak height) was 1.025 seconds, the time $T_2$ was 1.228 seconds, and the time $T_3$ was 1.336 seconds.

Some sample components may not appear in the destructive analysis, but do appear as peaks in the fraction collector flow detector. The upstream detector 13 may be particularly useful for identification of these peaks.

The system can be automated, once the system time delay parameters are established. Particularly, a computer with suitable conventional software can record, among other system parameters, the time intervals between detection at the destructive detector (e.g., MS) and detection at the fraction collection detector, and between the upstream detector and the MS. Delay times can be automatically computed from these time intervals, and can be used to dynamically control the fraction collection and to characterize the contents of collected fractions. In an exemplary embodiment, the computer receives a signal from each of the detectors, indicating arrival at each detector of a sample component; establishes a time for the respective arrivals, and employs a calibrated delay interval either to predict the arrival of a sample component at the fraction collector and to activate the fraction collector to collect a fraction of the eluent flow at the predicted time, or (where the fraction collector is in a continuous-collection mode) to identify the aliquot in the collection series that is collected at the predicted time and is therefore expected to contain the sample component. The computer can be programmed to identify desired sample components according to one or more known characteristics of the signal at one or more of the detectors, and can activate the fraction collector only at the predicted arrival times for the desired sample components. For example, where the destructive detector is a mass spectrometer the computer can be programmed to recognize a particular m/z signal or combination of m/z signals from the destructive detector, and to activate the fraction collector at the predicted arrival time for sample components containing the particular signal or signals. Or, the computer can be programmed to activate the collector only when a delay calculations indicate that a sample component of interest in the eluent stream is arriving at the fraction collector, and to avoid collection of eluent flow between peaks, not containing sample components of interest.

A calibrant can be introduced into the eluent flow upstream from the splitter at any time during analysis of eluent from the column, and employed to recalibrate the system. Recalibrated delay times can then be employed in the automatic calculation of arrival times, allowing for correction of predictions as flow parameters of the system change over the course of the analytical run.

Figure 4:
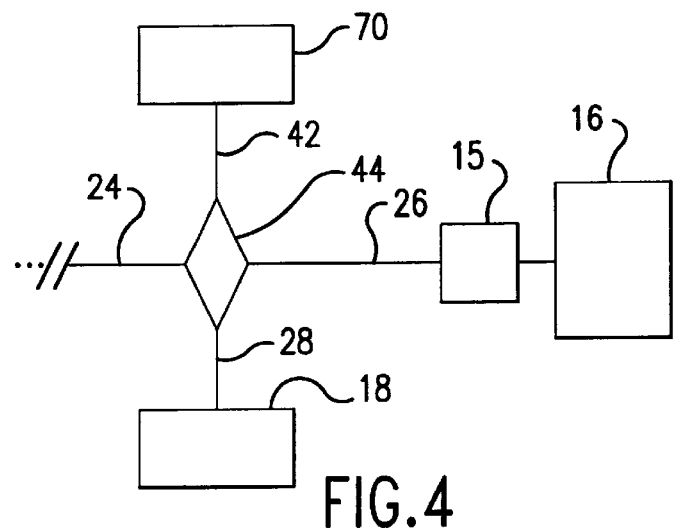
FIGS. 4, 5, and 6 are flow path diagrams showing arrangements of components of alternative exemplary fraction collection delay calibration apparatus according to the invention.
Figure 5:
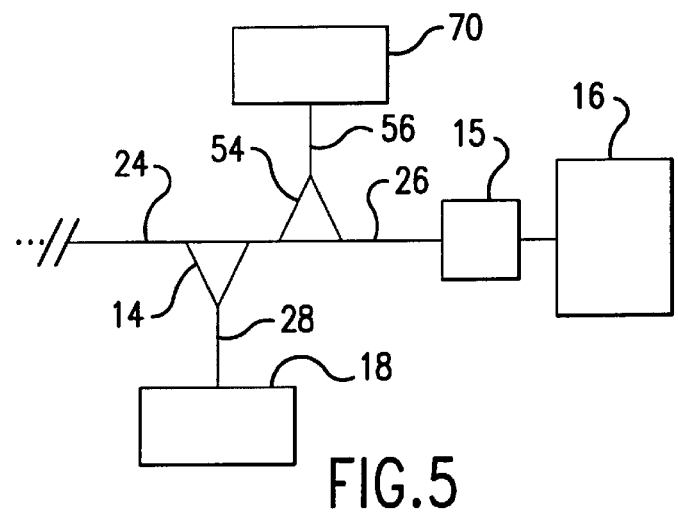
Figure 6:
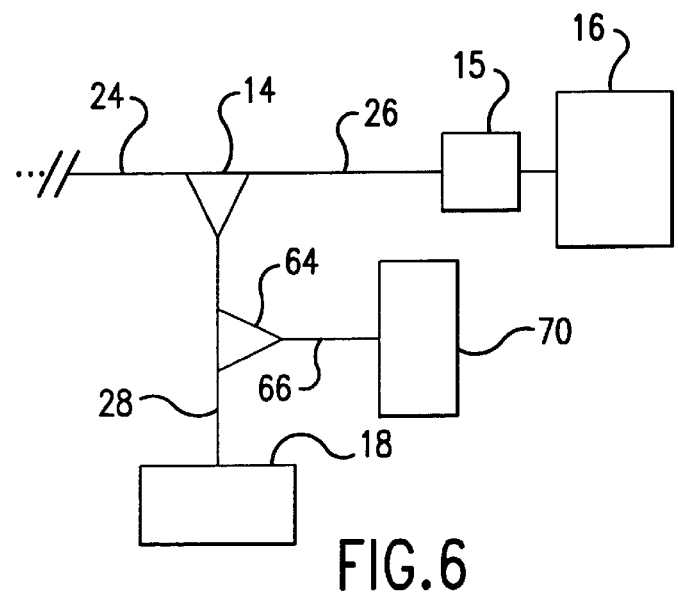

Referring now to FIGS. 4–6, there are shown diagrammatically parts of system flow paths generally indicated at 40, 50, 60, in which an additional conduit is provided, to direct a part of the eluent stream to a quantitative detector 70. In each of these Figs., the part of the system upstream from the splitter may be configured, for example, as in either of FIG. 1 or 2, and like parts are identified with like reference numerals. In the embodiment of FIG. 4, the splitter 44 has a third outlet, and the additional conduit 42 is connected at its upstream end to the third outlet and at its downstream end to the quantitative detector 70. In the embodiment of FIG. 5, an additional splitter 54 is interposed in conduit 26 between splitter 14 and flow detector 15. Splitter 54 receives eluent from the splitter 14 and directs the eluent flow in part by way of conduit 26 to the fraction collector 16 and in part by way of an additional conduit 56 to the quantitative detector 70. Accordingly, in such embodiments the portion of the eluent stream that is directed from the splitter toward the fraction collector 16 is diverted to the quantitative detector 70. In the embodiment of FIG. 6, an additional splitter 64 is interposed in conduit 28 between splitter 14 and destructive analytical detector 18. Splitter 64 receives eluent from the splitter 14 and directs the eluent flow in part by way of conduit 28 to the destructive analytical detector 18 and in part by way of an additional conduit 66 to the quantitative detector 70. Accordingly, in such embodiments the portion of the eluent stream that is directed from the splitter toward destructive analytical detector 18 is diverted to the quantitative detector 70. The quantitative detector is a destructive detector, and may be, for example, an evaporative light-scattering detector or a nitrogen-sulfur detector; such detectors are known in the chromatography art. The respective components of the separated sample typically will have different arrival times at the quantitative detector 70, at the destructive detector 18 and at the fraction collector 16, as described generally above with reference to FIGS. 1 and 2. A delay interval between the time of arrival at the quantitative detector 70 and the time of arrival at any of the other detectors can be determined and calibrated in a similar fashion, to provide for association of the quantitative data generated at the quantitative detector with a particular sample component.

Embodiments other than those described in detail above, and various modifications of the particular embodiments described above, will be apparent to the person of ordinary skill, and such modifications and other embodiments are within the following claims.

What is claimed is:

1. A method for collecting a sample component in a sample stream from an LC column comprising dividing the sample stream into a first stream passing to a destructive detector and a second stream passing to a sample collector, introducing a calibrant into the sample stream and determining the difference in time $T_D$ between the time of detection of the calibrant at the destructive detector and the time of detection of the calibrant at a nondestructive detector near the sample collector, and detecting the sample component in the first stream using the destructive detector and determining the time $T_2$ at which the sample component was detected by the destructive detector, and collecting the sample component at a time $T_3$ equivalent to $T_D+T_2$.

2. A method for calibrating an expected time of arrival at a collector of a sample component in a sample stream from an LC column, comprising dividing the sample stream into a first stream passing into a destructive detector and a second stream passing to a sample collector, introducing a calibrant into the sample stream and determining the difference in time $T_D$ between the time of detection of the calibrant at the destructive detector and the time of detection of the calibrant at a nondestructive detector near the sample collector, whereby a sample component detected at the destructive detector at a time $T_2$ is expected to arrive at the sample collector at a time $T_D$ later than $T_2$.

* * * * *